United States Patent [19]

Christie

[11] Patent Number: 4,591,356
[45] Date of Patent: May 27, 1986

[54] INTRAVENOUS NEEDLE STABILIZING BAND

[76] Inventor: Barbara C. Christie, 3096 Westwood Way, Alpharetta, Ga. 30201

[21] Appl. No.: 617,894

[22] Filed: Jun. 6, 1984

[51] Int. Cl.$^4$ .............................................. B61M 5/32
[52] U.S. Cl. ............................ 604/179; 128/DIG. 26
[58] Field of Search ............................... 604/174, 179; 128/DIG. 26

[56] References Cited

U.S. PATENT DOCUMENTS

| | | | |
|---|---|---|---|
| 2,409,432 | 2/1945 | Hubbard | 604/179 |
| 3,059,645 | 10/1962 | Hasbrouck et al. | 604/179 |
| 3,726,280 | 4/1973 | Lacount | 604/179 |
| 3,765,421 | 10/1973 | Poprik | 604/179 |
| 3,878,849 | 4/1975 | Muller et al. | 604/179 |
| 3,918,446 | 11/1975 | Buttaravoli | 128/DIG. 26 |
| 3,926,185 | 12/1975 | Krzewinski | 128/DIG. 26 |
| 4,088,136 | 5/1978 | Hasslinger et al. | 604/179 |
| 4,096,863 | 6/1978 | Kaplan et al. | 604/179 |
| 4,275,721 | 6/1981 | Olson | 128/DIG. 26 |
| 4,316,461 | 2/1982 | Marais et al. | 604/179 |
| 4,336,806 | 6/1982 | Eldridge, Jr. | 604/174 |
| 4,445,894 | 5/1984 | Kovacs | 604/179 |
| 4,470,410 | 9/1984 | Elliott | 128/DIG. 26 |
| 4,490,141 | 12/1984 | Lako et al. | 128/DIG. 26 |

FOREIGN PATENT DOCUMENTS 556668 12/1974 Sweden ............................. 604/179

*Primary Examiner*—Paul J. Hirsch
*Attorney, Agent, or Firm*—Walter Leuca; Richard G. Kinney

[57] ABSTRACT

An arm band for stabilizing an intravenous needle inserted into a patient's vein. The arm band is provided with a hole in the body thereof, spaced from a side edge of the band. The hole is dimensioned to surround the needle. The band is further formed with a slit from a side edge thereof to the hole, to provide opposing flaps which open to permit passage over the tube part of the inserted intravenous needle. A strip is secured at one end thereof to the band on one side of the slit. The free end of the strip is extended over the slit, causing the edge of the hole to surround the needle. The free end of the strip is provided with means to secure it to the band on the other side of the slit, thereby obtaining the stabilization of the intravenous needle.

9 Claims, 3 Drawing Figures

INTRAVENOUS NEEDLE STABILIZING BAND

BACKGROUND OF THE INVENTION

1. Field of the Invention

This invention relates to means for securing an intravenous needle inserted in a patient's vein.

2. Description of the Prior Art

The prior art method of securing an intravenous needle inserted in a patient's vein is by taping the needle hub and part of the tube adjacent to the needle hub to the skin surrounding the needle. It is very difficult to provide a smooth and secure connection between the adhesive tape, the needle and the adjacent skin, since intravenous needles are normally inserted at an angle to the body; that is, in the arm where an intravenous needle is normally inserted. Since such intravenous needles are normally inserted into veins, any small movement of the arm or tube of the intravenous needle will disturb the needle part in the vein, which will cause pain and bruises. Periodic removal and replacement of the adhesive tape also results in considerable discomfort.

SUMMARY OF THE INVENTION

In accordance with the present invention, an easily changed bandage for stabilizing an intravenous needle that may be inserted into a patient's limb comprises a longitudinal, flexible strip having no skin adhesives, sized to fit about the patient's limb. The strip defines a hole sized to closely fit about the needle. A slit through the strip is defined laterally from the hole to one side of the strip.

Means, such as a second strip, for releasably connecting the two sides of the slit together, so as to open and close the slit, are provided. And means for releasably affixing the strip about the patient's limb is also provided.

These as well as other objects and advantages will become more apparent upon a careful study of the following detail description of this invention when read with reference to the accompanying drawings which illustrate a preferred embodiment thereof.

Figure 1:
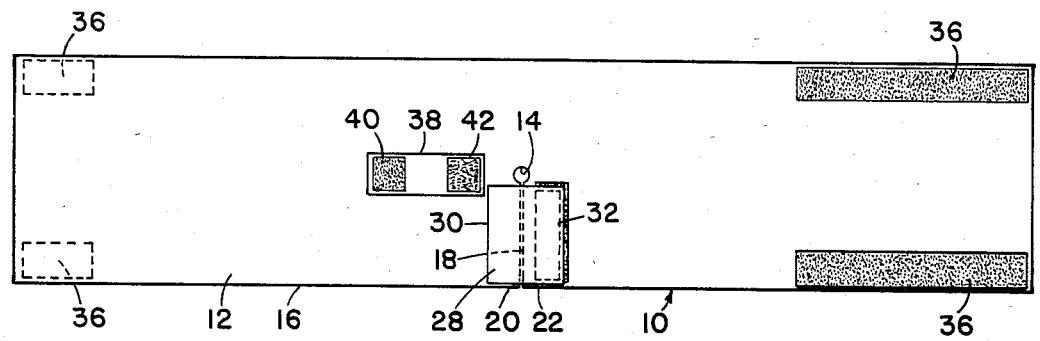
FIG. 1 is a top view of the intravenous needle stabilizer of this invention, showing the band in longitudinal layout.
Figure 2:
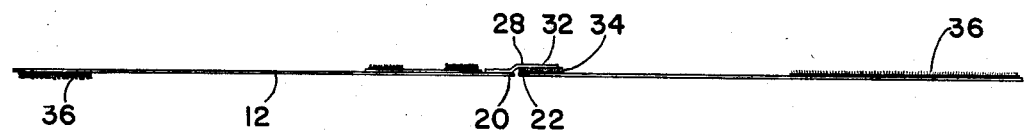
FIG. 2 is a side edge view of FIG. 1.
Figure 3:
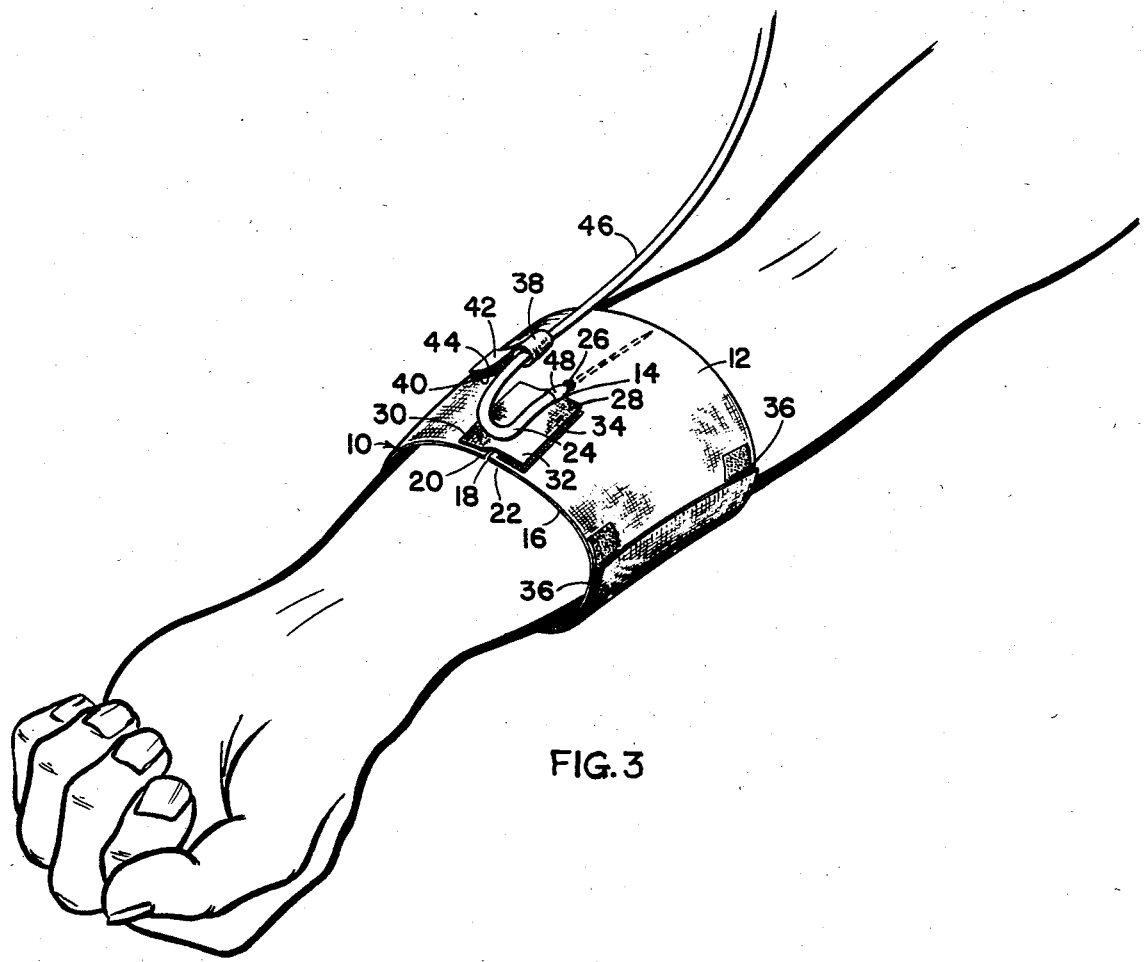
FIG. 3 is a perspective view of this invention, shown encircled around the arm of a patient, serving to secure an stabilize an intravenous needle. CL DETAILED DESCRIPTION OF THE INVENTION Referring now more particularly to the drawings wherein the preferred embodiment of this invention is illustrated, reference numeral 10 designates this invention generally. It comprises a strip 12 of flexible material of a nature suitable to comfortably encircle a patient's limb. A hole or fenestra 14 is provided in the body of the strip 12, spaced from side edge 16. A slit or cut 18 is made from side edge 16 to fenstra 14, forming opposing flaps 20 and 22 which when unsecured provide an opening for allowing passage therethrough of tube part 24 of intravenous needle 26. A second strip 28 of like material is provided on strip 12, one end thereof being fixed to strip 12 at one side of slit 18, as at 30, and the other end thereof being free to extend to the other side of slit 18, as at 32, overlapping slit 18. I provide connecting means such as mating Velcro strips 34 on strip 12 and free end 32 of second strip 28, to removably secure free end 32 to strip 12, to overlap and maintain slit 18 close beneath the tube part 24 of needle 26. I also provide connecting means such as mating Velcro patches 36 to secure the encirclement of strip 12 around the patient's arm. I further provide a third strip 38 on the body of strip 12 at any suitable location. One end 40 of strip 36 is secured to strip 12, and the other end 42 thereof being free. Connecting means are provided at the fixed and free ends, preferably means such as mating Velcro patches 44, to allow the ends thereof to be removably connected together upon forming a loop, by doubling back free end 42 to encircle the extended body 46 of tube part 24.

In the operation of my invention, the intravenous needle 26 is inserted into the patient's vein in the conventional manner. The strip 12 of this invention is positioned over the patient's arm, aligning hole 14 over the base of intravenous needle 26, adjacent hub 48, and slit 18, being longitudinally aligned over the tube part 24 of intravenous needle 26 so that, upon wrapping the ends of strip 12 around the patient's arm, opposing flap members 20 and 22 will give way, allowing hole 14 to surround needle 26 adjacent hub 48, and allowing tube part 24 to pass through slit 18 without disturbing the inserted needle. By securing the ends of strip 12 together, the encircling edge of hole 14 firmly surrounds intravenous needle 26 at the base thereof adjacent hub 48. Needle 26 is thus effectively and easily secured and immobilized. The free end 32 of second strip 28 is pulled over slit 18 underneath tube part 24 of intravenous needle 26 and is secured to strip 12 on the other side of slit 18 by any convenient means, preferably with Velcro strip connectors 34. Free end 42 of third strip 38 is made to loop around the extended body 46 of tube part 24 of intravenous needle 16, thereby immobilizing it, preventing motion which may move the needle.

It is now obvious from the above detail description that my invention is a simple, economical to manufacture and easy to apply arm band which effectively stabilizes and immobilizes an intravenous needle inserted into a patient'vein.

I claim:

1. An easily changed non-skin-adhesive band for stabilizing an intravenous needle inserted in a patient's vein on a limb of the patient comprising:

a longitudinal flexible strip having ends connectable together, said strip having a hole in the body thereof and being cut laterally therethrough from said hole to the side edge of said strip to form a slit, said hole sized to fit closely about the intravenous needle;

a second flexible strip having one end thereof fixed to said longitudinal strip adjacent one side of said cut, and the other end of said second strip being free to extend said second strip over said cut so as to close the slit, whereby an intravenous needle may be first inserted into the patient and thereafter stablized by attaching the band by positioning the hole of the strip on the needle portion entering the skin, passing the needle and attached tube through the slit, thereafter overlapping the second strip to close said slit and surround and stablize the needle with the longitudinal flexible strip wrapped around the limb and its ends secured together, and whereby the stabilizer may be thereafter easily changed without removal of or disturbance of the needle.

2. The arm band of claim 1 wherein the ends of said longitudinal strip are further characterized as having means for connecting said ends together.

3. An arm band for stabilizing an intravenous needle inserted in a patient's vein comprising:
  a longitudinal flexible strip, having no skin adhesive, said strip having a hole in the body thereof said hole being sized to closely fit about the intravenous needle and having a slit laterally therethrough from said hole to a side edge of said strip;
  a second strip having one end thereof fixed to said longitudinal strip adjacent one side of said slit, and the other end of said second strip being free to extend said second strip over said slit; and
  means on the other side of said slit to secure said free end of said second strip to said longitudinal strip.

4. The arm band of claim 3 wherein the ends of said longitudinal strip are further characterized as having means for connecting said ends together.

5. An easily changed arm band for stabilizing an intravenous needle inserted in a patient's vein without the need for removing the needle when changing the band comprising:
  a longitudinal strip having ends connectable together, said strip having a hole in the body thereof and a slit laterally therethrough from the hole to a side edge thereof said hole being sized to closely surround the intravenous needle and said strip being free of skin-adhesive so that it can be applied and removed without directly adhering to or disturbing the skin;
  a second strip having one end thereof fixed to said longitudinal strip adjacent one side of said slit, and the other end of said second strip being free to extend said second strip over said slit;
  means on said free end of said second strip and on said longitudinal strip to connect said free end to said longitudinal strip; and
  a third strip, one end thereof being fixed to said longitudinal strip and the other end thereof being free to form a loop.

6. The arm band of claim 5 wherein the free end of said third strip is further characterized as being connectable to said longitudinal strip.

7. An easily used intravenous needle and tube stabilizing bandage that may be easily changed without removal or disturbance of the needle or tube inserted into the limb of a patient comprising:
  an elongated flexible strip sized to wrap about a limb into which an intravenous needle and tube are inserted, said strip having a hole defined therein at a distance from both edges and defining a slit from one edge to the hole, said hole being sized to closely surround the needle at the point of insertion into the limb, and said strip not being secured to the skin by adhesive,
  means for releasably connecting the two sides of the slit together so as to selectively close and open the slit, and
  means for releasably connecting the elongated flexible strip when so wrapped around the limb so as to releasably secure it to the limb.

8. The invention of claim 7 wherein said strip include means affixed to its outer surface for also holding a portion of the tube in position above the strip.

9. The invention of claim 7 wherein said means for closing includes loop and hook fasteners.

* * * * *